United States Patent [19]

Werner

[11] 4,357,274

[45] Nov. 2, 1982

[54] PROCESS FOR THE MANUFACTURE OF SCLERO PROTEIN TRANSPLANTS WITH INCREASED BIOLOGICAL STABILITY

[75] Inventor: Heinz-Helmut Werner, Melsungen, Fed. Rep. of Germany

[73] Assignee: Intermedicat GmbH, Emmenbrucke, Switzerland

[21] Appl. No.: 290,519

[22] Filed: Aug. 6, 1981

[51] Int. Cl.$^3$ .......................... C07G 7/00; C08H 1/00; C08H 1/06
[52] U.S. Cl. ........................... 260/123.7; 128/DIG. 8
[58] Field of Search ...................................... 260/123.7

[56] References Cited

U.S. PATENT DOCUMENTS

| | | | |
|---|---|---|---|
| 2,649,357 | 8/1953 | Happey et al. | 260/123.7 |
| 2,928,822 | 3/1960 | Johnsen et al. | 260/117 |
| 3,073,702 | 1/1963 | Keil et al. | 260/123.7 X |
| 3,239,420 | 3/1966 | Gonshery et al. | 260/123.7 X |
| 3,308,113 | 3/1967 | Johnsen et al. | 260/123.7 X |
| 3,475,404 | 10/1969 | Johnsen et al. | 260/123.7 |
| 4,264,493 | 4/1981 | Battista | 260/123.7 X |

*Primary Examiner*—Howard E. Schain
*Attorney, Agent, or Firm*—Merriam, Marshall & Bicknell

[57] ABSTRACT

In a process for the manufacture of sclero protein transplants in which raw sclero protein from humans or animals is watered, treated with $H_2O_2$, degreased, rinsed, dried and sterilized, the improvement in which the sclero protein, after rinsing and prior to drying, is treated with glycerin or polyethylene glycol.

8 Claims, 1 Drawing Figure

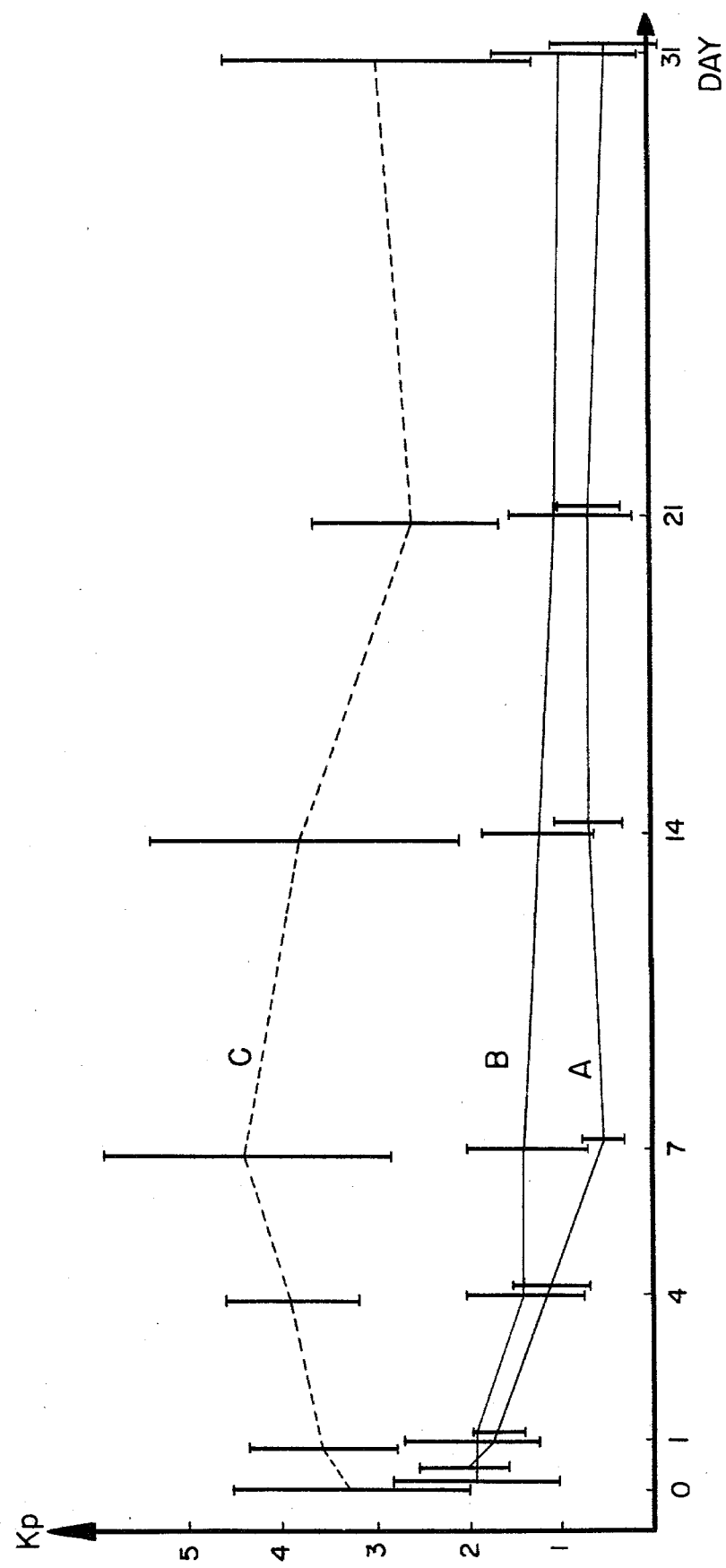

PROCESS FOR THE MANUFACTURE OF SCLERO PROTEIN TRANSPLANTS WITH INCREASED BIOLOGICAL STABILITY

It has been known that some sclero proteins as, for example, collagen, keratin, and elastin can be transplanted homologously as well as heterologously in humans and in animals, in order to alleviate an existing deficiency of natural body tissues. The receiving organism is able to recognize, more or less well depending on the type of implant, that a foreign protein is present. As a rule, decomposition of the implanted substance takes place. In a few cases, decomposition of the implant is so slow that the body simultaneously is able to produce new binding tissue. At this point we refer to the "guide track principle" as it has been described, for example, in German Pat. No. 20 04 553.8-09.

It is understandable that the "guide track principle" must fail when tissue production is slower than tissue decomposition. Therefore, as a rule, an increased resistance against tissue decomposition activity induced by the body is desirable. Thus, use of the lyophilized hard cerebral meninges of the human as a transplant is almost essential in neurosurgery. However, other collagens, which are obtained from animals, play a useful role.

The brochure published by B. Braun Melsungen AG: "Lyodura ® for the Homoi Plastic Replacement of Body Structures" in 1978, and the numerous literature references mentioned therein, establish the importance and usefulness placed on implantable sclero proteins in the medical field.

Presently, freeze-drying and acetone drying are the principal methods used in preparing transplants from sclero proteins. However, the biological stability of the products thereby obtained is often unsatisfactory, especially when used in replacing the mechanically stressed organs as, for example, fasciae, bands, and tendons. If the stability of the implant decreases faster in the body than the new structure which is produced by the body in healing the wound, a successful operation is not achieved and the patient suffers corresponding harm.

An object of the invention is to provide a process by which the biological stability of the sclero protein transplants is improved.

By experimental tests, we found, surprisingly, that the resistance of sclero proteins to biological decomposition can be substantially improved by a modified drying process.

The attached drawing constitutes a graph which shows, for example, the advantage obtained by using the process of the invention. The drawing illustrates the change in the tensile strength of 10 mm wide strips of hard cerebral meninges of the human after implantation beneath the skin on the back of rabbits. 210 of those strips were implanted and taken out at various times after the operation to measure the tensile strength of the strips. The curve A was derived from tests with acetone dried cerebral meninges, curve B with freeze-dried cerebral meninges and curve C with cerebral meninges which had been manufactured according to the process of the invention.

While the curves in the drawing show there was no significant difference in the tensile strength between the products produced by acetone drying and freeze drying during the thirty-one day observation period, the material manufactured according to the invention showed an increase in tensile strength by a factor of 1.7 to 7.0.

The desired characteristics can be achieved by introducing the sclero protein material into a glycerin solution, after prior conventional procedural steps of purifying and antigen separation. Water is removed from the material in the glycerin. Simultaneously, glycerin impregnates the transplant by a diffusion process. During the subsequent drying process the percentage content of glycerin increases substantially. Similar results can be obtained with polyethylene glycol having a molecular weight of about 400 to 2000.

Glycerin or polyethylene glycol which has diffused into the sclero protein material acts as a protective factor during freezing. However, this fact, which has been known as such, is not responsible for the increased biological stability after it is used as an implantation, for it became evident that the freeze drying can be substituted by air drying at room temperature without adversely affecting the resistance which the sclero protein has against decomposition in a living organism.

The process is carried out in that one first wets the sclero proteins as, for example, collagen, keratin, elastin from humans or animals and, in particular, raw dura matter from humans, with water in the usual way. Then one treats it with $H_2O_2$, thereafter one degreases it, rinses it with water, dries and sterilizes it, but wherein, according to the invention, the glycerin or polyethylene glycol treatment step is inserted between the rinsing and drying steps.

The glycerin can be used in a 5% to 50% by weight, preferably in a 20% to 40% solution, in water. A 30% glycerin solution in water is particularly useful.

Polyethylene glycol useful in the process has a molecular weight of about 400 to 2000 and it is usually used in a 5% to 50% by weight polyethylene glycol, in particular in a 20% to 40% solution, in water.

The following advantages over the prior art are achieved by the process according to the invention:

The product is soft and no rehydration is necessary prior to its use.

The product is transparent; for example, during brain operations one can see the fluid and the brain surface through the transplant.

The product has increased biological stability.

The process according to the invention is explained in detail by means of the following example describing the manufacture of soft dry dura.

EXAMPLE

Raw dura matter which was supplied in concentrated NaCl was watered for 24 hours. Thereupon it was put into 2% to 20%, preferably 5%, $H_2O_2$ for 48 hours. Then the dura matter was degreased in a Soxhlet apparatus in acetone-diethylether 1:1 for 4 hours. The degreased dura matter was rinsed for 12 to 24 hours with water.

The dura matter treated in this way was stirred for 4 hours in a 30% glycerin solution in water. The moist dura matter which was obtained was freeze dried in a lyophilizer. As an alternative, the moist dura matter was dried at room temperature in the open air.

After drying for 12 hours, the soft dry dura matter was taken out and sterilized with 2.5 Mrad. The dura matter was soft, transparent and had increased biological stability. The dura matter obtained according to the processes known up to now was substantially harder, not transparent and had a lower biological stability.

The following data in connection with the attached drawing show the surprising results of the comparative tests.

Tabular Chart of the Tensile Strength of the Dura Strips (Width 10 mm) after Implantation. Data in Kp, (n = 10 per group, each point of the curve in the drawing is based on 10 individual measurements).

| Implantation Time (days) | Lyodura Obtained by Freeze Drying | Tutoplast Obtained by Acetone Drying | Soft Dura According to the Invention |
|---|---|---|---|
| 0 | 1.9 ± 0.9 | 2.0 ± 0.5 | 3.2 ± 1.3 |
|   | 100% ± 47 | 105% ± 26 | 168% ± 68 |
| 1 | 1.9 ± 1.7 | 1.7 ± 0.3 | 3.5 ± 0.9 |
|   | 100% ± 37 | 89% ± 16 | 184% ± 47 |
| 4 | 1.4 ± 0.6 | 1.2 ± 0.4 | 3.9 ± 0.7 |
|   | 74% ± 32 | 63% ± 21 | 205% ± 37 |
| 7 | 1.4 ± 0.6 | 0.7 ± 0.3 | 4.4 ± 1.6 |
|   | 74% ± 32 | 37% ± 16 | 232% ± 84 |
| 14 | 1.3 ± 0.6 | 0.7 ± 0.4 | 3.8 ± 1.7 |
|   | 68% ± 32 | 37% ± 21 | 200% ± 90 |
| 21 | 1.0 ± 0.5 | 0.7 ± 0.3 | 2.6 ± 1.0 |
|   | 53% ± 26 | 37% ± 16 | 137% ± 53 |
| 31 | 0.9 ± 0.8 | 0.4 ± 0.6 | 2.8 ± 1.7 |
|   | 47% ± 42 | 21% ± 32 | 147% ± 90 |

Second line = data in %
O-value Lyodura = 100%

The soft dura matter obtained according to the invention can be used as transplants in various areas of medical use which are well known to those skilled in the art. A great number of those areas of use are mentioned on page 2 in the above-named brochure of the firm B. Braun Melsungen.

What is claimed is:

1. In a process for the manufacture of sclero protein transplants in which raw sclero protein from humans or animals is watered, treated with $H_2O_2$, degreased, rinsed, dried and sterilized, the improvement in which the sclero protein, after rinsing and prior to drying, is treated with glycerin or polyethylene glycol.

2. The improved process according to claim 1 in which a 5% to 50% glycerin solution in water is used.

3. The improved process according to claim 1 in which polyethylene glycol having a molecular weight of about 400 to 2000 is used.

4. The improved process according to claim 1 or 3 in which a 5% to 50% polyethylene glycol solution in water is used.

5. The improved process according to any one of claims 1 to 3 in which the sclero protein used is collagen, keratin or elastin from humans or from animals.

6. The improved process according to any one of claims 1 to 3 in which the sclero protein used is dura from humans.

7. The improved process according to claim 6 in which a 20% to 40% glycerin solution in water is used.

8. The improved process according to claim 7 in which a 30% glycerin solution in water is used.

* * * * *